(12) United States Patent
Gradel (10) Patent No.: US 9,173,740 B2
(45) Date of Patent: *Nov. 3, 2015

(54) METHOD FOR PRODUCING A CERAMIC ACETABULUM

(75) Inventor: Thomas Gradel, Marignier (FR)

(73) Assignee: Inventorio SA, Gland (CH)

( * ) Notice: Subject to any disclaimer, the term of this patent is extended or adjusted under 35 U.S.C. 154(b) by 326 days.

This patent is subject to a terminal disclaimer.

(21) Appl. No.: 13/703,637

(22) PCT Filed: Jun. 17, 2011

(86) PCT No.: PCT/IB2011/052649
§ 371 (c)(1),
(2), (4) Date: Jan. 7, 2013

(87) PCT Pub. No.: WO2011/158213
PCT Pub. Date: Dec. 22, 2011

(65) Prior Publication Data
US 2013/0091683 A1    Apr. 18, 2013

(30) Foreign Application Priority Data

Jun. 17, 2010 (FR) ..................... 10 54834

(51) Int. Cl.
*A61B 17/58* (2006.01)
*A61F 2/00* (2006.01)
(Continued)

(52) U.S. Cl.
CPC ... *A61F 2/32* (2013.01); *A61F 2/34* (2013.01); *A61F 2/4609* (2013.01); *A61F 2/4607* (2013.01);
(Continued)

(58) Field of Classification Search
CPC ..... A61F 2/30723; A61F 2/4609; A61F 2/32; A61F 2/34; A61F 2002/3446; A61F 2002/4629; A61F 2310/00179; A61F 2002/30487; A61F 2/4607; A61F 2002/30077; Y10T 29/49826; Y10T 29/49813; Y10T 29/49815; Y10T 29/49853; Y10T 29/49863; Y10T 29/49908; Y10T 29/49909; Y10T 29/49911; Y10T 29/49913
USPC .................. 29/446, 447, 450, 453, 456, 800; 623/22.24, 22.27, 22.28, 22.29; 606/91
See application file for complete search history.

(56) References Cited

U.S. PATENT DOCUMENTS 4,362,681 A * 12/1982 Spector et al. ............... 264/112
4,563,778 A * 1/1986 Roche et al. ............ 623/22.38
(Continued)

FOREIGN PATENT DOCUMENTS

DE   3101333 A1   12/1981
DE   4403994 C1   10/1995
(Continued)

*Primary Examiner* — Essama Omgba
*Assistant Examiner* — Darrell C Ford
(74) *Attorney, Agent, or Firm* — William H. Eilberg (57) ABSTRACT

A method for producing a prosthetic acetabulum includes the following steps. First, one makes available a ceramic cup (1) that has a concave internal receiving face (3) and has an external annular receiving structure (6). Next, one makes available a placement and orientation insert (7) that has an annular peripheral fixing structure (10) designed to cooperate with the receiving face (9) of the external annular receiving structure (6) by engaging around the external annular receiving structure (6). Next, one heats the placement and orientation insert (7) in order to increase the dimensions of the insert. Next, one engages the annular peripheral fixing structure (10) around the receiving face (9) of the external annular receiving structure (6). Finally, one returns the placement and orientation insert (7) to ambient temperature in order to reduce the dimensions of the insert, in such a way as to obtain a radial clamping of the annular peripheral fixing structure (10) on the external annular receiving structure (6).

16 Claims, 8 Drawing Sheets

(51) Int. Cl.
*A61F 2/32* (2006.01)
*A61F 2/34* (2006.01)
*B23P 11/02* (2006.01)
*A61F 2/46* (2006.01)
*A61F 2/30* (2006.01)

(52) U.S. Cl.
CPC .......... *A61F 2002/30077* (2013.01); *A61F 2002/30487* (2013.01); *A61F 2002/3446* (2013.01); *A61F 2002/4629* (2013.01); *A61F 2310/00179* (2013.01); *Y10T 29/49826* (2015.01)

(56) References Cited

U.S. PATENT DOCUMENTS

| | | | | |
|---|---|---|---|---|
| 4,566,138 A * | 1/1986 | Lewis et al. | | 623/22.38 |
| 5,080,677 A * | 1/1992 | Shelley | | 623/22.24 |
| 5,486,181 A | 1/1996 | Cohen | | |
| 5,658,346 A * | 8/1997 | Willi | | 623/22.24 |
| 5,702,476 A * | 12/1997 | Limacher et al. | | 623/22.28 |
| 5,702,478 A * | 12/1997 | Tornier | | 623/22.24 |
| 5,888,205 A | 3/1999 | Pratt | | |
| 6,132,469 A * | 10/2000 | Schroeder | | 623/22.24 |
| 6,468,281 B1 | 10/2002 | Badorf et al. | | 606/91 |
| 6,488,713 B1 * | 12/2002 | Hershberger | | 623/22.11 |
| 6,589,284 B1 * | 7/2003 | Silberer | | 623/22.29 |
| 6,610,097 B2 * | 8/2003 | Serbousek et al. | | 623/22.24 |
| 6,682,567 B1 * | 1/2004 | Schroeder | | 623/22.24 |
| 6,966,932 B1 * | 11/2005 | Schroeder | | 623/22.19 |
| 6,988,015 B1 * | 1/2006 | Schopf et al. | | 700/98 |
| 7,597,715 B2 * | 10/2009 | Brown et al. | | 623/22.32 |
| 7,635,447 B2 * | 12/2009 | Hamman et al. | | 419/2 |
| 7,727,282 B2 * | 6/2010 | Slone et al. | | 623/22.12 |
| 8,066,778 B2 * | 11/2011 | Meridew et al. | | 623/22.32 |
| 8,123,815 B2 * | 2/2012 | Meridew et al. | | 623/22.29 |
| 8,287,915 B2 * | 10/2012 | Clineff et al. | | 424/602 |
| 8,585,769 B2 * | 11/2013 | Vankoski et al. | | 623/22.24 |
| 8,764,843 B2 * | 7/2014 | Gradel | | 623/22.12 |
| 8,900,319 B2 * | 12/2014 | Morrey et al. | | 623/22.24 |
| 8,968,414 B2 * | 3/2015 | Armacost et al. | | 623/22.28 |
| 2003/0050705 A1 * | 3/2003 | Cueille et al. | | 623/22.24 |
| 2004/0019380 A1 * | 1/2004 | Baege et al. | | 623/11.11 |
| 2004/0117023 A1 * | 6/2004 | Gerbec et al. | | 623/18.11 |
| 2007/0122305 A1 * | 5/2007 | Lambert et al. | | 422/4 |
| 2008/0255568 A1 * | 10/2008 | Tornier et al. | | 606/91 |
| 2009/0192610 A1 * | 7/2009 | Case et al. | | 623/16.11 |
| 2009/0234459 A1 * | 9/2009 | Sporring et al. | | 623/18.11 |
| 2009/0265009 A1 * | 10/2009 | Ward et al. | | 623/18.11 |
| 2010/0174380 A1 * | 7/2010 | Lewis | | 623/22.11 |
| 2012/0180300 A1 * | 7/2012 | Gradel | | 29/447 |
| 2012/0303035 A1 * | 11/2012 | Geebelen | | 606/91 |
| 2013/0059011 A1 * | 3/2013 | Clineff et al. | | 424/602 |
| 2013/0131741 A1 * | 5/2013 | Kourtis et al. | | 606/86 R |
| 2013/0131823 A1 * | 5/2013 | Morrey et al. | | 623/22.24 |
| 2013/0245781 A1 * | 9/2013 | Allen et al. | | 623/22.28 |
| 2014/0066812 A1 * | 3/2014 | Song et al. | | 600/590 |
| 2014/0309749 A1 * | 10/2014 | Taylor et al. | | 623/22.32 |
| 2014/0336776 A1 * | 11/2014 | Taylor et al. | | 623/22.21 |
| 2015/0039091 A1 * | 2/2015 | Grostefon et al. | | 623/22.18 |

FOREIGN PATENT DOCUMENTS

| | | |
|---|---|---|
| EP | 0931523 A1 | 7/1999 |
| EP | 1721586 A1 | 11/2006 |
| FR | 2830746 A1 | 4/2003 |
| FR | 2897527 A1 | 2/2006 |
| FR | 2909541 A1 | 6/2008 |
| WO | 2009098491 A1 | 8/2009 |
| WO | 2010146398 A1 | 12/2010 |

* cited by examiner

METHOD FOR PRODUCING A CERAMIC ACETABULUM

TECHNICAL FIELD OF THE INVENTION

The present invention relates to a method for producing a prosthetic acetabulum intended to replace the natural acetabulum of the hip.

A total hip prosthesis comprises two parts constituting a ball-and-socket joint, namely a female part intended to replace the natural acetabulum of the hip, and a male part intended to replace the head of the femur. The male part of the joint generally has a shaft which is intended to engage in the medullary canal of the femur and of which the proximal end is connected by a neck to a spherical prosthetic head intended to engage in the female part. The female part of the joint, which has to replace the natural acetabulum of the hip, usually comprises a cup with a convex outer anchoring face, which is accommodated in a prepared acetabular cavity in the pelvic bone. This cup has a concave receiving face intended to directly or indirectly receive the spherical prosthetic head.

When fitting the cup in the acetabular cavity, it must be possible to use an impactor for holding and manipulating the cup and for applying a force to drive the cup into the acetabular cavity of the bone with a good orientation and, in particular, for a long enough period to allow a cement to set between the outer surface of the insertion cup and the acetabular cavity of the bone.

When the cup is made of metal, such a material allows means to be easily provided for reliable fixing of an impactor. To this end, the document U.S. Pat. No. 5,486,181 describes fixing an impactor by means of fins, while the document U.S. Pat. No. 5,888,205 describes a threaded top hole formed in the concave receiving face.

In the particular case of a cup made entirely of ceramic, these solutions are not applicable. This is because ceramic is too fragile for the formation of fins or of a threaded hole. A threaded hole is also unacceptable since, in the case of a cup made of ceramic, the concave receiving face is intended to receive the spherical prosthetic head directly: the concave receiving face must therefore be perfectly smooth and cannot therefore have the slightest machining.

The documents EP 0 931 523 and FR 2 830 746 describe impactors intended to be fixed to a cup by way of pivoting fastening fingers. The document WO 2009/098491 describes an impactor intended to be fixed to a cup by way of rotary bayonets. All of these impactors are complex and cumbersome and do not provide particularly good retention of the cup.

The document FR 2 909 541 describes a cup with a convex and hemispherical outer anchoring face. To hold this cup during its impaction, an outer annular groove is provided near its free annular edge. This annular groove permits the fixation of an impactor comprising a main body with at least two hook-shaped elastic tabs. In this document, the force with which the cup is retained by the impactor is in correlation with and substantially equal to the force that has to be applied to spread apart the elastic tabs. This means that the better the hold of the cup by the impactor, the more difficult it is to spread the tabs apart, and this causes the user more effort to fix the impactor to the cup. This increases the risk of accidental damage to the cup, which is critical in the case of a cup made of ceramic, which is a fragile material.

There is a need to permit easy fixation of an impactor to a cup while providing a reliable hold of the cup.

SUMMARY OF THE INVENTION

A problem addressed by the invention is that of making available a method for producing a prosthetic hip acetabulum with a ceramic cup that can be fixed more reliably and more firmly to an impactor, while limiting the forces to be applied and avoiding any risk of contamination.

To achieve these objects, and others, the invention proposes a production method comprising the steps of:

a) providing a ceramic cup having a concave inner receiving face, and having an outer annular receiving structure, b) providing an installation and orientation insert having a peripheral annular fixing structure designed to cooperate with the receiving face of the outer annular receiving structure by engaging around the outer annular receiving structure, c) heating the installation and orientation insert in order to increase the dimensions thereof, d) engaging the peripheral annular fixing structure around the receiving face of the outer annular receiving structure, e) bringing the installation and orientation insert back to room temperature in order to reduce the dimensions thereof, so as to achieve a radial clamping of the peripheral annular fixing structure on the outer annular receiving structure.

Such a production method makes it possible to obtain satisfactory radial clamping of the installation and orientation insert on the ceramic cup, and effective retention of the installation insert on the ceramic cup.

The forced retention of the installation and orientation insert on the insertion cup by radial clamping ensures reliable and secure fixation, by means of which it is possible to withstand the forces applied during the impaction of the insertion cup. The radial clamping of the peripheral annular fixing structure on the outer annular receiving structure makes it possible to achieve this reliable fixation without over-complicating the shape of the outer annular receiving structure.

The retention of the installation and orientation insert on the insertion cup is very reliable, especially by virtue of the fact that the radial clamping takes place on an annular receiving structure which is external and which thus has a large contact surface with the installation and orientation insert.

Finally, the radial clamping of the peripheral annular fixing structure on the outer annular receiving structure induces a state of prestressing in the ceramic cup, and this prestressing limits the risks of breaking of the cup during its impaction in the acetabulum of the pelvis of a patient, but also during its transport and its handling when the method according to the invention is implemented in the factory.

When the installation and orientation insert is mounted on the cup in the factory, the surgeon then only has to fix the impactor on the installation and orientation insert in order to proceed with the impaction of the cup. There is no risk of the surgeon damaging the concave inner receiving face of the insertion cup, the latter being protected by the installation and orientation insert.

It must be emphasized that fixing the installation and orientation insert to the cup by means of expansion of the installation and orientation insert by heating (followed by a return to room temperature) is particularly advantageous compared to a first alternative solution that would involve cooling the cup rather than the installation and orientation insert in order to reduce the external dimensions thereof (followed by a return to room temperature) or compared to a second alternative solution that would involve engaging the installation and orientation insert inside the cup and cooling this installation and orientation insert in order to reduce the external dimensions thereof (followed by a return to room temperature).

Indeed, these alternative solutions necessitate a refrigerated enclosure in which a condensation phenomenon can take place, leading to the presence of condensate liquids on the cup or the installation and orientation insert, which liquids may be contaminated by bacteria or microbes. This is particularly critical when the installation and orientation insert is made of plastic: the plastics that can be used for the installation and orientation insert, for example polyethylene, have a tendency to absorb the liquids. This is also particularly critical when the cup is made of ceramic, for example like the cup from the document U.S. Pat. No. 6,682,567, which has layers of porous ceramic, the pores of which can absorb and retain liquids. There is therefore a risk that the installation and orientation inserts made of plastic and/or the cups made of ceramic absorb condensate liquids that are contaminated by bacteria or microbes, which then leads to the contamination of the prosthetic acetabulum.

Since the receiving structure is annular, it allows the cup to be oriented in any direction by the application of radial forces to the impactor in any possible direction.

Since the receiving structure is external, the concave inner receiving face can be perfectly smooth, in order to permit perfect sliding between the cup and the spherical prosthetic head.

Advantageously, the method can also have a step f) during which the unit thus formed and packed in a microbial protection envelope is sterilized.

Preferably, provision can be made that the step f) of sterilization is carried out by bombardment with gamma rays, preferably at a dose of between approximately 25 kGy and approximately 40 kGy.

In order to ensure perfect mobility of the prosthesis, it is important that the receiving structure does not limit the clearance of the prosthetic neck.

Moreover, the prosthetic neck supporting the spherical prosthetic head is generally made of a very strong material (for example metal), whereas the ceramic of the cup is a very hard but fragile material. As a result, any contact or shock between the prosthetic neck and the ceramic of the cup would damage the latter irremediably and must therefore be avoided.

To do this, provision can advantageously be made that:
the concave inner receiving face is a sphere portion having an opening face contained in an opening plane,
the annular receiving structure is set back from the opening plane.

By virtue of the fact that the annular receiving structure for the fixation of the impactor is set back from the opening plane, i.e. offset in the direction of the summit of the convex outer anchoring face, this annular receiving structure does not limit the angular clearance of the prosthetic femoral shaft that will be fitted. At the same time, this limits the risk of contact between the prosthetic femoral shaft and the edge of the ceramic cup, which therefore reduces the risk of damage to or breakage of the cup.

Advantageously, provision can be made that:
the outer annular receiving structure comprises a continuous or interrupted peripheral radial shoulder of the annular edge, with a receiving face directed toward the outside,
the installation and orientation insert has a continuous or interrupted peripheral annular fixing structure with a connecting face directed toward the inside and designed to cooperate with the receiving face of the outer annular receiving structure.

Such an outer annular receiving structure is relatively simple to produce.

According to a first variant, provision can be made that:
the receiving face of the outer annular receiving structure has an interrupted peripheral locking groove,
the connecting face of the peripheral annular fixing structure of the installation and orientation insert has a plurality of locking ribs which are distributed peripherally and are designed so as to engage in the interrupted peripheral locking groove.

According to a second variant, provision can be made that:
either the receiving face of the outer annular receiving structure or the connecting face of the peripheral annular fixing structure has a continuous peripheral annular locking groove,
the other of the connecting face of the peripheral annular fixing structure or the receiving face of the outer annular receiving structure has a continuous or interrupted peripheral annular locking rib designed so as to engage in the continuous peripheral annular locking groove.

The locking groove and the locking rib or ribs participate in retaining the installation and orientation insert on the cup. This also greatly increases the strength of the connection between the installation and orientation insert and the insertion cup, so as to withstand the orientation couples that are transmitted by the surgeon by means of the impactor.

Advantageously, provision can be made that:
the peripheral radial shoulder of the annular edge has a thickness of greater than or equal to approximately 0.5 mm,
said interrupted peripheral locking groove or said continuous peripheral annular locking groove of the outer annular receiving structure has a radial thickness of between approximately 0.2 mm and approximately 0.6 mm.

Such dimensions are compatible with a ceramic cup having a small thickness near its upper annular edge, for example of approximately 3 mm. In other words, these dimensions are such that they do not weaken or do not greatly weaken the ceramic cup near its upper annular edge, while at the same time they permit a good hold of the installation and orientation insert. The use of a cup having a small thickness near its upper annular edge (for example a thickness of approximately 3 mm) makes it possible to increase the diameter of the spherical head of the male part of the joint and thus effectively limit the risk of dislocation.

Preferably, provision can be made that the peripheral radial shoulder of the annular edge has a height of between approximately 1 mm and approximately 4 mm.

Such a height of the peripheral radial shoulder provides a sufficient contact surface between the installation and orientation insert and the ceramic cup for the radial clamping, without thereby excessively diminishing the surface area of the convex outer anchoring face intended to come into contact with the bone. This is all the greater in view of the fact that the outer anchoring surface part situated substantially in the vicinity of the equatorial plane thereof is a part that participates substantially in the retention of the insertion cup in the acetabular cavity of the pelvis.

Advantageously, provision can be made that said interrupted peripheral locking groove or said continuous peripheral annular locking groove of the outer annular receiving structure has a height of between approximately 0.4 mm and approximately 3 mm.

Preferably, provision can be made that the installation and orientation insert and the outer annular receiving structure of the cup are designed in such a way that, when the installation and orientation insert is fixed on the outer annular receiving structure of the cup, the installation and orientation insert does not protrude outside a substantially hemispherical surface defined by the outer convex anchoring face of the cup. This therefore avoids any risk of conflict of the installation and orientation insert with the bone substance present near the prepared acetabular cavity of the pelvis of the patient.

Advantageously, the peripheral annular fixing structure of the installation and orientation insert can have a radial thickness substantially equal to or less than the thickness of the radial shoulder of the annular edge.

Preferably, the installation and orientation insert can be made of polyethylene. Polyethylene is commonly used in the medical field and is inexpensive and easy to machine. Moreover, polyethylene does not risk damaging the ceramic cup when the surgeon applies shocks to the impactor in order to insert the cup in the acetabular cavity of the patient.

Advantageously, the installation and orientation insert can have an assembly structure to which an impactor can be removably fixed.

Preferably, the assembly structure can comprise a fixation hole with internal thread made in the installation and orientation insert, permitting the screwing of a corresponding threaded portion of the impactor.

Advantageously, the fixation hole can be a through-hole able to cooperate with a disconnecting tool that has a threaded rod able to be screwed into the through-hole and which has a distal end designed to bear against the concave inner receiving face of the cup when the threaded rod is screwed into the through-hole.

Preferably, provision can be made that:
the installation and orientation insert is designed in such a way that a free space remains between the installation and orientation insert and the bottom of the concave inner receiving face once the installation and orientation insert has been fixed to the outer annular receiving structure of the cup,
the installation and orientation insert bears in a sealed manner across its connecting face against the receiving face of the outer annular receiving structure,
the fixation hole is a through-hole via which the free space between the installation and orientation insert and the bottom of the concave inner receiving face is brought into communication with the outside and which is dimensioned for leaktight engagement of the end of a syringe.

BRIEF DESCRIPTION OF THE DRAWINGS

Other subjects, features and advantages of the present invention will become clear from the following description of particular variants, said description making reference to the attached figures, amongst which.

Some of the attached figures illustrate a subject matter that is not part of the present invention but that is described below and that may become the subject of an independent protection. These figures are the following.

DESCRIPTION OF PREFERRED EMBODIMENTS

Each one of FIGS. 1, 4, 5 and 8 shows a ceramic cup 1 of a prosthetic hip acetabulum. This ceramic cup 1 comprises:
a convex outer anchoring face 2, designed to be anchored in an acetabular cavity of the pelvis of a patient, and a concave inner receiving face 3 with an annular edge 4,
an annular receiving structure 6 designed in such a way that an impactor can be fixed to said annular receiving structure 6 for the impaction of the cup 1 in the acetabular cavity of the pelvis of a patient.

The receiving structure 6 is external, which means that the concave inner receiving face 3 can be perfectly smooth in order to permit perfect sliding between the cup and the spherical prosthetic head.

It can be seen more particularly that:
the concave inner receiving face 3 is a sphere portion having an opening face 5 contained in an opening plane P,
the annular receiving structure 6 is set back from the opening plane P.

In other words, the annular receiving structure 6 is offset with respect to the opening plane P, in the direction of the summit S of the outer anchoring face 2.

The annular receiving structure 6 is therefore not situated in the continuation of the inner receiving face 3 (which is at the most hemispherical) continuing the latter past the summit S. It is thus possible to avoid limiting the angular clearance of the prosthetic neck, and the risk of contact between the prosthetic neck stem and the annular edge 4 of the ceramic cup 1 is reduced.

Figure 1:
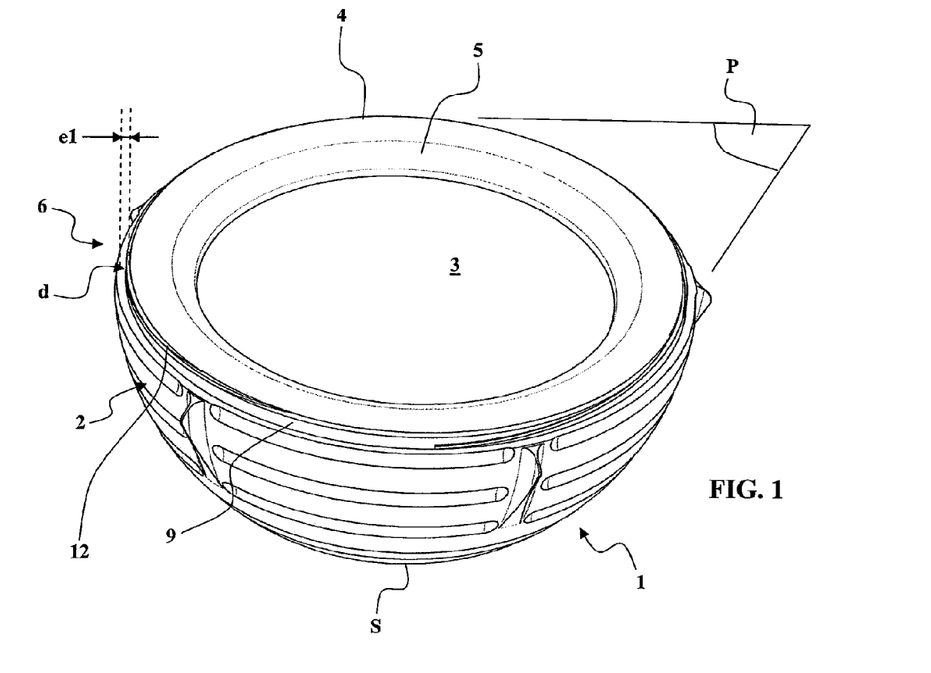
FIG. 1, which is a perspective view of a ceramic cup of a prosthetic acetabulum.
Figure 2:
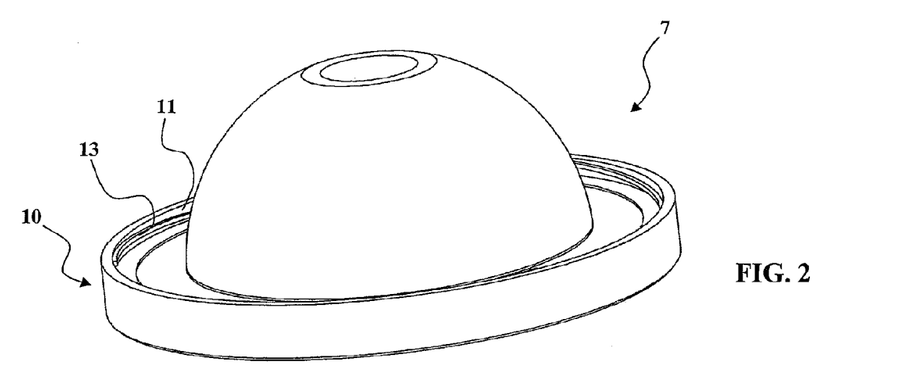
FIG. 2, which is a perspective view of an installation and orientation insert intended to be joined to the cup from FIG. 1.
Figure 3:
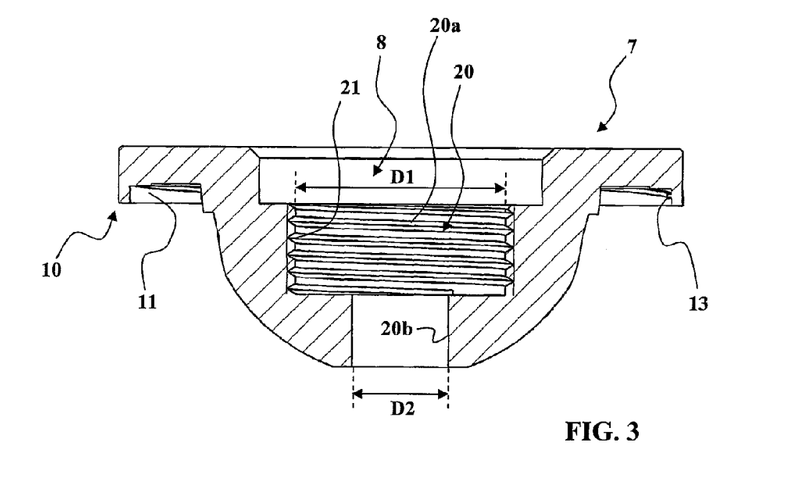
FIG. 3, which is a sectional view of the installation and orientation insert from FIG. 2.
Figure 4:
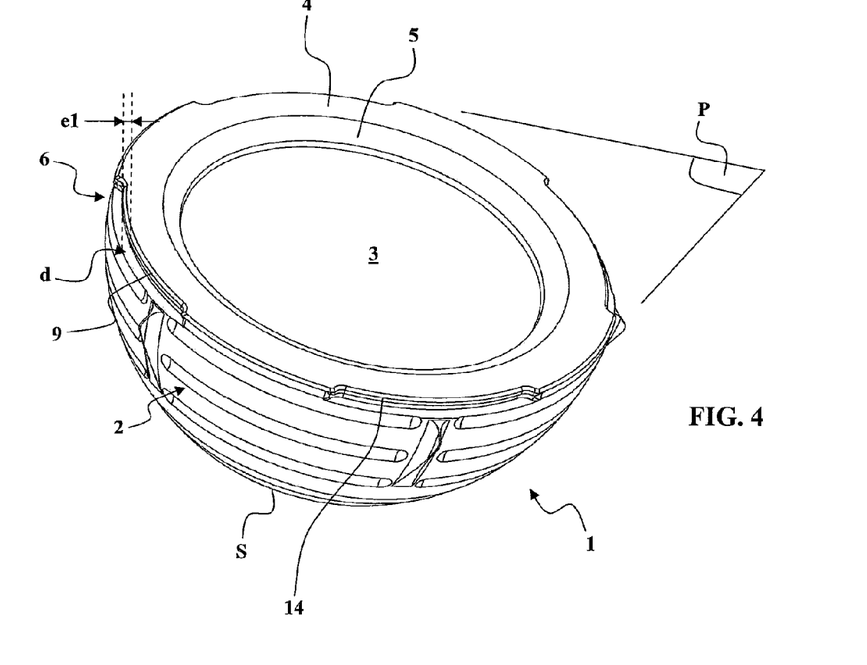
FIG. 4 is a perspective view of a ceramic cup of a prosthetic acetabulum according to a first variant of the invention.
Figure 5:
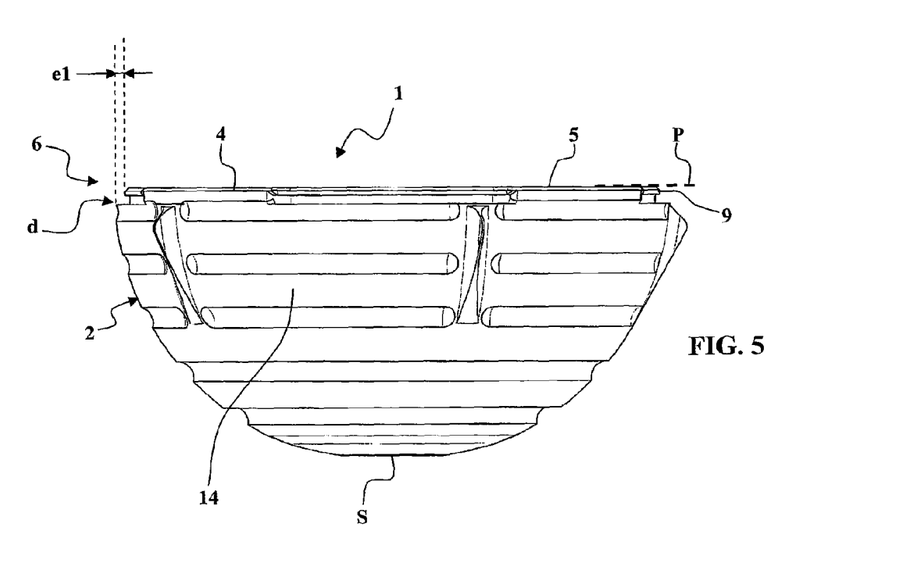
FIG. 5 is a side view of the ceramic cup from FIG. 4.
Figure 6:
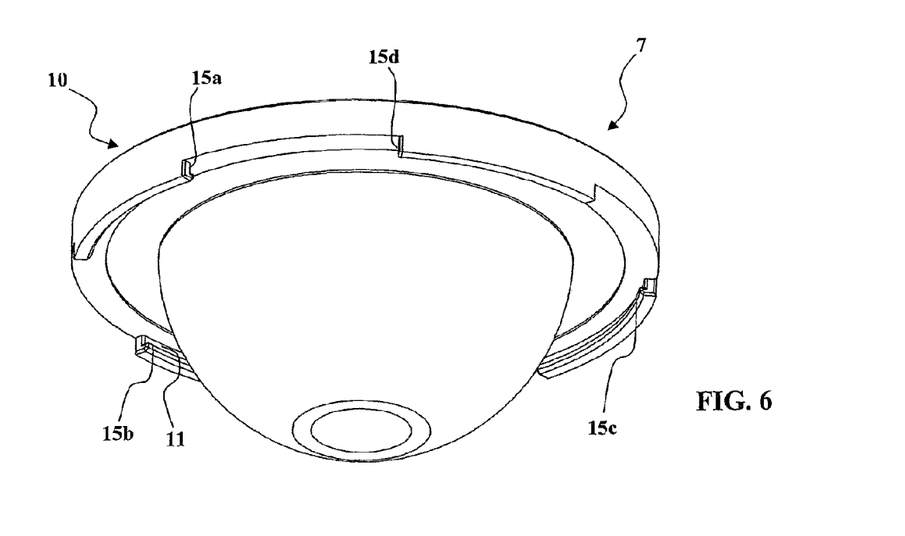
FIG. 6 is a perspective view of an installation and orientation insert intended to be joined to the ceramic cup from FIGS. 4 and 5.
Figure 7:
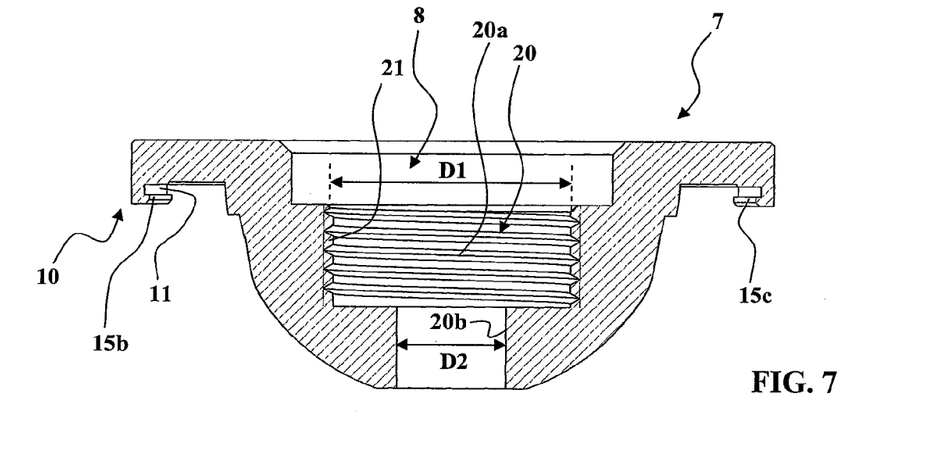
FIG. 7 is a sectional view of the installation and orientation insert from FIG. 6.
Figure 8:
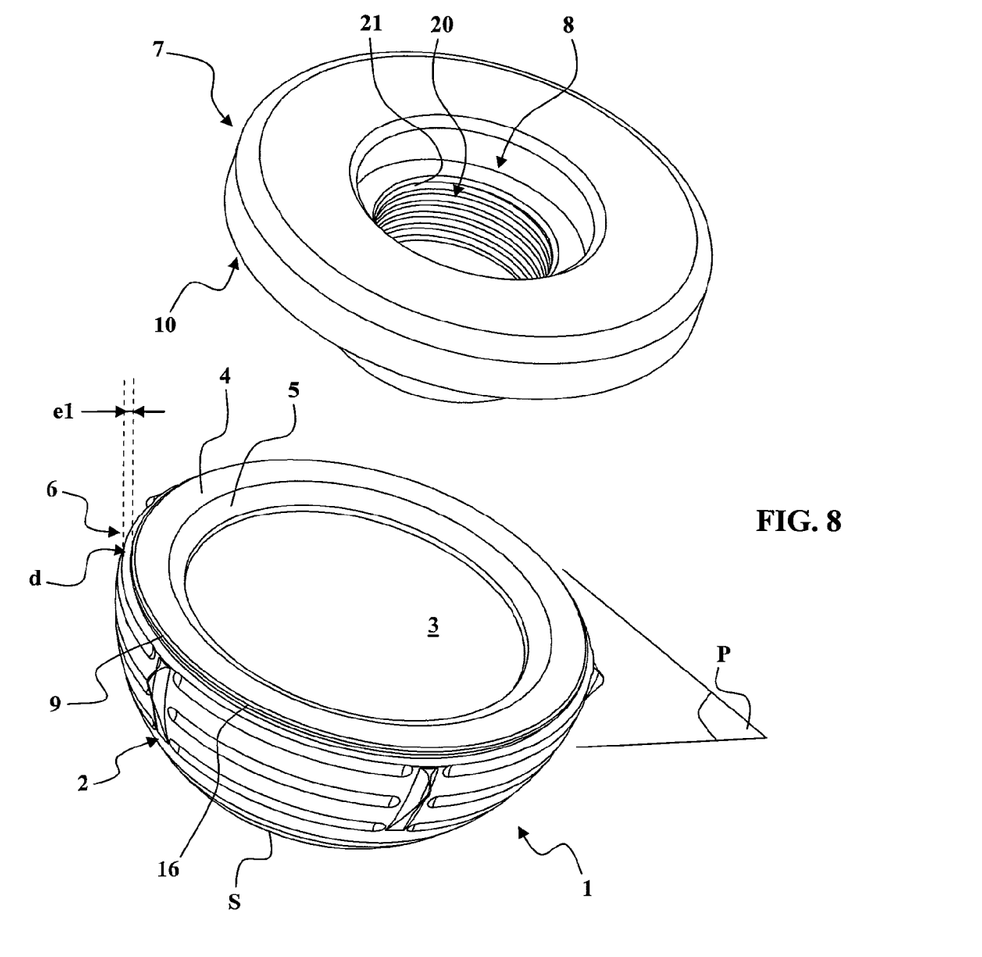
FIG. 8 is a perspective view of an installation and orientation insert and of a ceramic cup of a prosthetic hip acetabulum according to a second variant of the invention.
Figure 9:
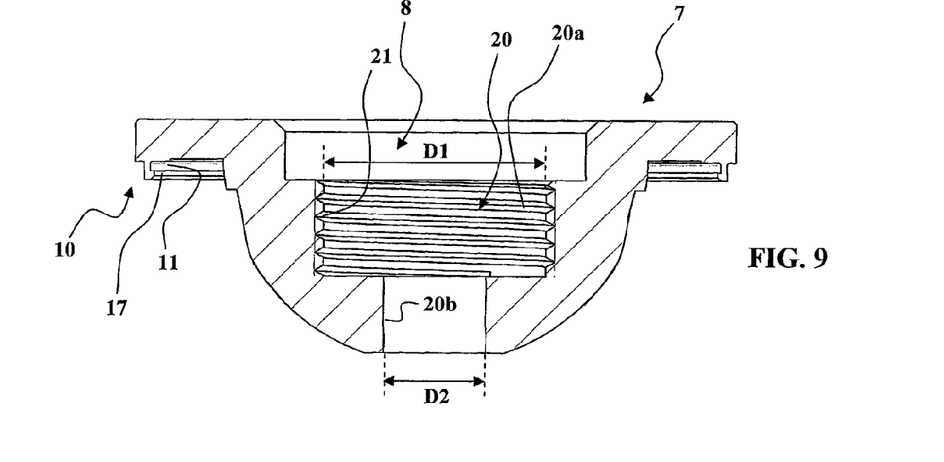
FIG. 9 is a sectional view of the installation and orientation insert from FIG. 8.

FIGS. 2, 3, 6, 7 and 9 show an installation and orientation insert 7 intended to be joined to a cup 1. The installation and orientation insert 7 of FIGS. 2 and 3 is intended to be joined to the cup 1 from FIG. 1. The installation and orientation insert 7 of FIGS. 6 and 7 is intended to be joined to the cup 1 from FIGS. 4 and 5 or FIG. 8. The installation and orientation insert 7 of FIG. 9 is intended to be joined to the cup 1 from FIG. 8.

Each installation and orientation insert 7 can be fixed removably to the outer annular receiving structure 6 of the cup 1 and has an assembly structure 8 on which an impactor can be removably fixed.

In FIGS. 1, 5 and 8, it can be seen that the outer annular receiving structure 6 comprises a continuous or interrupted peripheral radial shoulder d of the annular edge 4, with a receiving face 9 directed toward the outside. It can be seen in FIGS. 2, 3, 6, 7 and 9 that each installation and orientation insert 7 has a continuous or interrupted peripheral annular fixing structure 10 with a connecting face 11 directed toward the inside and designed to cooperate with the receiving face 9 of the outer annular receiving structure 6.

In the subject matter of FIGS. 1 to 3, the receiving face 9 of the outer annular receiving structure 6 has an external thread 12, while the connecting face 11 of the peripheral annular fixing structure 10 of the installation and orientation insert 7 has an internal thread 13 designed to cooperate with the external thread 12 by screwing.

The subject matter of the present invention is illustrated in FIGS. 4 to 13. On these figures, the outer annular receiving structure 6 and the peripheral annular fixing structure 10 are designed in such a way that the installation and orientation insert 7 is engaged with force around the outer annular receiving structure 6 and is retained forcibly by a radial clamping of the peripheral annular fixing structure 10 on the outer annular receiving structure 6.

On account of the external nature of the annular receiving structure 6, the contact surface between the installation and orientation insert 7 and the cup 1, on which surface the clamping is exerted, is large. This results in excellent fixation of the installation and orientation insert 7 on the cup 1.

In order to further improve the hold of the installation and orientation insert 7 on the cup 1, a supplementary cooperation can be provided between the installation and orientation insert 7 and the cup 1 by means of one or more locking ribs that engage in a locking groove.

In a first variant, illustrated on FIGS. 4 to 7, provision is made that:
the receiving face 9 of the outer annular receiving structure 6 has an interrupted peripheral locking groove 14,
the connecting face 11 of the peripheral annular fixing structure 10 of the installation and orientation insert 7 has a plurality of locking ribs 15a to 15d which are distributed about the periphery and are designed so as to engage in the interrupted peripheral locking groove 14.

In a second variant, illustrated on FIGS. 8 and 9, the receiving face 9 of the outer annular receiving structure 6 has a continuous peripheral annular locking groove 16, while the connecting face 11 of the peripheral annular fixing structure 10 has a continuous peripheral annular locking rib 17 designed so as to engage in the continuous peripheral annular locking groove 16.

In this second variant, it is also possible that the connecting face 11 of the peripheral annular fixing structure 10 has an interrupted peripheral annular locking rib. The installation and orientation insert 7 can then be similar to that of the first variant, illustrated on FIGS. 6 and 7.

Figure 10:
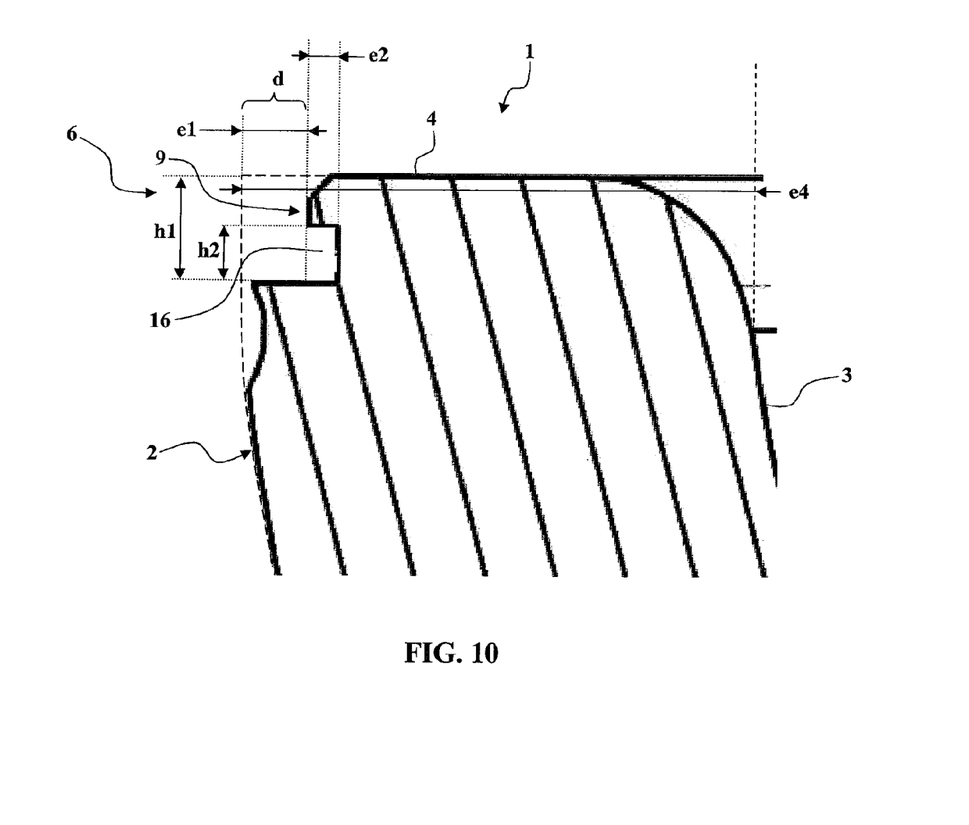
FIG. 10 is a partial sectional view of the ceramic cup from FIG. 8.

FIG. 10 is a partial sectional view of the annular edge 4 of the cup 1 from FIG. 8. It will be seen more particularly on FIG. 10 that the outer annular receiving structure 6 comprises a peripheral radial shoulder d with a receiving face 9 directed toward the outside. The peripheral radial shoulder d has a thickness e1 of greater than or equal to approximately 0.5 mm.

The receiving face 9 has the continuous peripheral annular locking groove 16. The continuous peripheral annular locking groove 16 has a radial thickness e2 of between approximately 0.2 mm and approximately 0.6 mm.

The ceramic cup 1 has a thickness e4 near its annular edge 4. The thickness e4 can be between approximately 3 mm and approximately 7 mm.

The peripheral radial shoulder d of the annular edge 4 has a height h1 of between approximately 1 mm and approximately 4 mm.

Finally, the continuous peripheral annular locking groove 16 has a height h2 of between approximately 0.4 mm and 3 mm.

All the dimensions given above in connection with the second variant are valid for the first variant and also for the subject matter of FIGS. 1 to 3.

Figure 11:
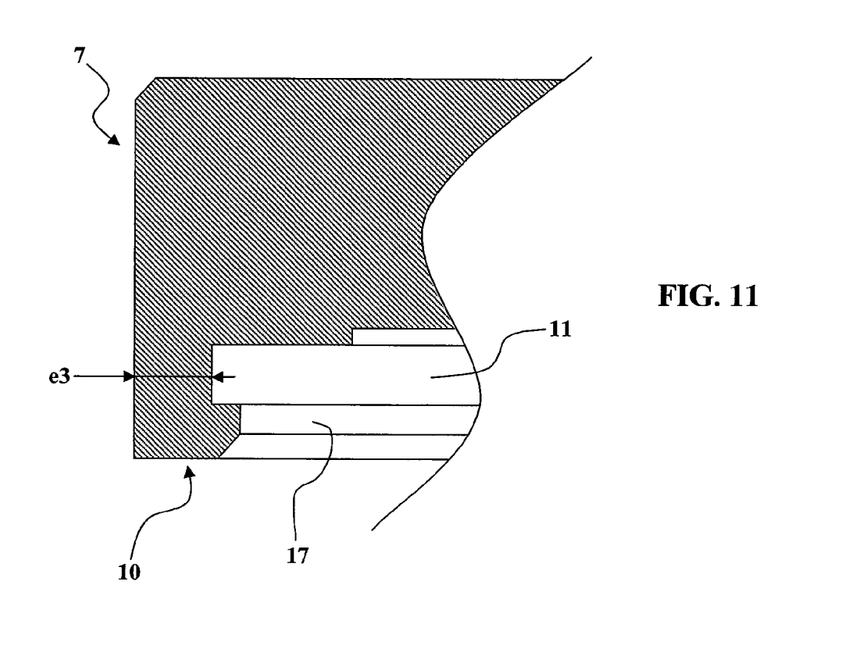
FIG. 11 is a partial sectional view of the installation and orientation insert from FIG. 9.
Figure 12:
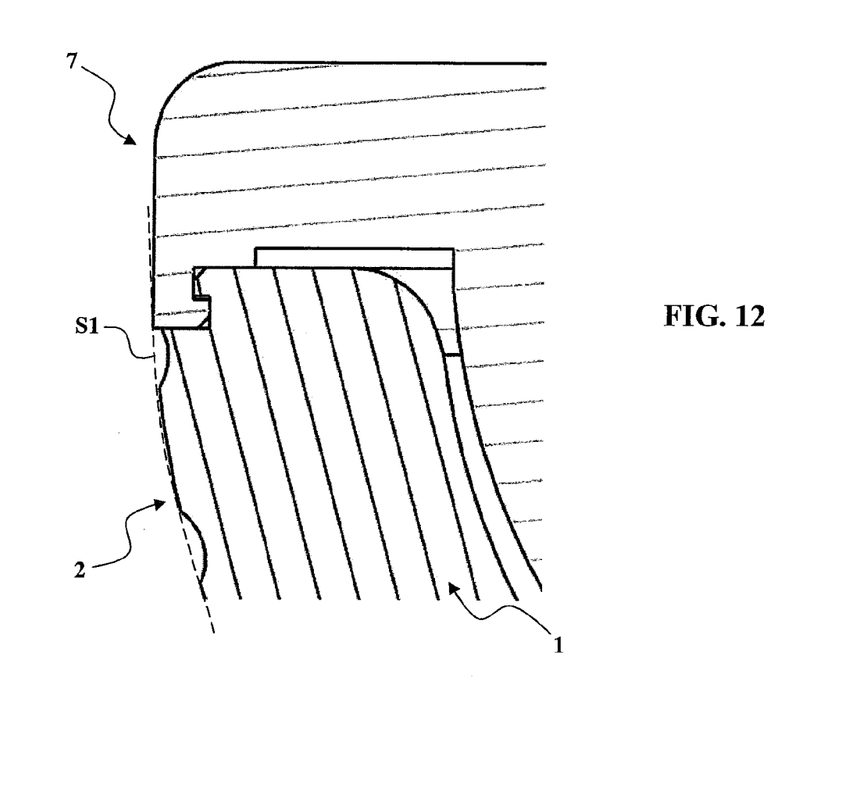
FIG. 12 is a partial sectional view of the ceramic cup and of the installation and orientation insert from FIGS. 10 and 11.

As can be seen on FIG. 11, the peripheral annular fixing structure 10 of the installation and orientation insert 7 has, with its connecting face 11 and its continuous peripheral annular locking rib 17, a shape and dimensions matching the receiving face 9 and the continuous peripheral annular locking groove 16. The installation and orientation insert 7 and the ceramic cup 1 can thus be joined very intimately, as is illustrated on FIG. 12.

In order to avoid any conflict of the installation and orientation insert 7 with the bone substance around the natural acetabular cavity of the pelvis of the patient, the installation and orientation insert 7 and the outer annular receiving structure 6 of the cup 1 are designed in such a way that, when the installation and orientation insert 7 is fixed to the outer annular receiving structure 6 of the cup 1, the installation and orientation insert 7 does not protrude outside a substantially hemispherical surface S1 (illustrated by broken lines on FIG. 12) defined by the convex outer anchoring face 2 of the cup 1. The outer anchoring face 2 is made substantially hemispherical in order to adapt to and fix reliably in the acetabular cavity of the patient.

To do this, the peripheral annular fixing structure 10 of the installation and orientation insert 7 has a radial thickness e3 (FIG. 11) substantially equal to or less than the thickness e1 of the radial shoulder d of the annular edge 4 (FIG. 10).

So as not to risk damaging the ceramic cup 1, the installation and orientation insert 7 is advantageously made of plastic, preferably of polyethylene, which is an inexpensive material, is easy to machine and avoids damage to the ceramic of the cup 1 despite the application of shocks to the impactor during the insertion of the cup 1 into the acetabular cavity of the patient.

Within the context of the invention, the concave inner receiving face 3 can be a slide face 3a for receiving the prosthetic femoral head. The concave inner receiving face 3 can also be a slide face 3a for receiving a movable articular insert, the movable articular insert pivotably receiving the prosthetic femoral head, for example for an acetabulum with dual mobility.

Figure 13:
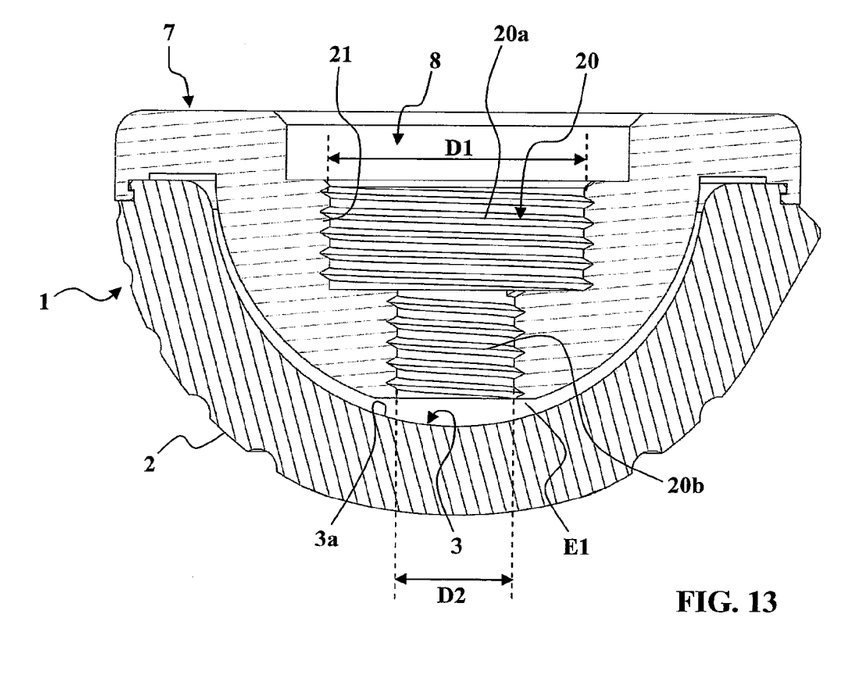
FIG. 13 is a sectional view of an insertion cup and of an installation and orientation insert once they have been assembled.

It can be seen more particularly on FIG. 13 that the assembly structure 8 of the installation and orientation insert 7 comprises a fixation hole 20 with internal thread 21. The internal thread 21 permits the screwing of a corresponding threaded portion of the impactor (not shown).

After the impaction of the ceramic cup 1 in the acetabular cavity of the pelvis of the patient, it is necessary to withdraw the installation and orientation insert 7. This withdrawal has to be performed without inducing appreciable stresses between the outer anchoring face 2 and the acetabular cavity of the pelvis of the patient, so as not to destroy the join made between them during the impaction.

A first solution to permit separation thus consists in the fixation hole 20 being a through-hole that is able to cooperate with a disconnecting tool having a threaded rod with a distal end designed to bear against the concave inner receiving face 3 of the cup 1 when the threaded rod is screwed into the through-hole. On FIG. 13, the fixation hole 20 has a first portion 20a of diameter D1 and a second portion 20b of smaller diameter D2. The threaded rod of the disconnecting tool has an external diameter designed such that it can be screwed into the portion 20b of diameter D2 of the fixation hole 20.

Alternatively, the threaded rod of the disconnecting tool can be accommodated slidably inside the impactor (which is screwed into the portion 20a) and thus has a diameter smaller than the diameter D2 of the portion 20b, in order to bear against the inner receiving face 3 by passing through the portion 20b.

A second solution permitting separation is one in which:
the installation and orientation insert 7 is designed such that a free space E1 remains between the installation and orientation insert 7 and the bottom of the concave inner receiving face 3 (FIG. 13) once the installation and orientation insert 7 has been fixed to the outer annular receiving structure 6 of the insertion cup 1, the installation and orientation insert 7 bears in a sealed manner across its connecting face 11 against the receiving face 9 of the outer annular receiving structure 6, the fixation hole 20 is a through-hole via which the free space E1 (provided between the installation and orientation insert 7 and the bottom of the concave inner receiving face 3) is brought into communication with the outside and which is dimensioned for leaktight engagement of the end of a syringe.

In the case of FIG. 13, the syringe end has an external diameter made for engaging in a leaktight manner in the portion of diameter D2 of the fixation hole 20.

By actuation of the syringe, a liquid such as water or physiological saline is thus injected at pressure into the free space E1 in order to induce a force of separation between the cup 1 and the installation and orientation insert 7.

In order to obtain a sealed contact between the installation and orientation insert 7 and the cup 1, use will preferably be made of the insertion cup 1 and the installation and orientation insert 7 that are illustrated on FIGS. 8 and 9.

Within the context of the present invention, when assembling the unit comprising the cup 1 and an installation and orientation insert 7, it is important not to damage the annular receiving structure 6 and the peripheral annular fixing structure 10. Thus, in order to achieve a radial clamping of the peripheral annular fixing structure 10 on the outer annular receiving structure 6, it is necessary that the peripheral annular fixing structure 10 has diameter dimensions equal to or less than those of the outer annular receiving structure 6.

An assembly method involving expansion and subsequent shrinkage is therefore used, during which the installation and orientation insert 7 is heated so as to increase its dimensions, after which the peripheral annular fixing structure 10 is engaged around the receiving face 9 of the outer annular receiving structure 6, and, finally, the installation and orientation insert 7 is brought back to room temperature in order to reduce its dimensions.

Such a method permits assembly without blunting or damaging the one or more locking ribs 15a-15d or 17, which thus retain sharp edges for a stronger connection between the installation and orientation insert 7 and the ceramic cup 1.

This method of production by heating does not involve any risk of contamination of the installation and orientation insert 7, especially when the latter is made of polyethylene.

On its return to room temperature, a radial clamping of the peripheral annular fixing structure 10 on the outer annular receiving structure 6 is obtained.

It is then possible to proceed to a step of sterilization of the unit thus formed and packed in a microbial protection envelope. A satisfactory sterilization will be achieved by bombardment with gamma rays, preferably at a dose of between approximately 25 kGy and approximately 40 kGy.

It is expressly underlined that the method of production and assembly of the unit on FIG. 13, by heating the installation and orientation insert 7 and then returning it to room temperature, can be used with a ceramic cup 1 whose outer annular receiving structure 6 is not necessarily situated set back from the opening plane P. The method of production may thus be able to be implemented independently of the position of the outer annular receiving structure 6 with respect to the opening plane P of the insertion cup 1.

The present invention is not limited to the embodiments that have been explicitly described, and instead it includes the variants and generalizations contained within the scope of the attached claims.

The invention claimed is:

1. A method for producing a prosthetic hip acetabulum, comprising the steps of:
   a) providing a ceramic cup (1) having a concave inner receiving face (3), having a convex outer anchoring face (2) designed to be anchored in an acetabular cavity of a pelvis of a patient, and having an outer annular receiving structure (6),
   b) providing an installation and orientation insert (7) having an assembly structure (8) on which an impactor can be removably fixed, and having a peripheral annular fixing structure (10) designed to cooperate with a receiving face (9) of the outer annular receiving structure (6) by engaging around the outer annular receiving structure (6), wherein the peripheral annular fixing structure (10) has an outer diameter which is not greater than an outer diameter of a substantially hemispherical surface (S1) defined by the ceramic cup (1), wherein the peripheral annular fixing structure (10) has a C-shaped cross-section which defines a connecting face (11) which is directed radially inwardly, and wherein the receiving face (9) of the outer annular receiving structure (6) is directed radially outwardly,
   c) heating the installation and orientation insert (7) in order to increase the dimensions thereof,
   d) engaging the peripheral annular fixing structure (10) around the receiving face (9) of the outer annular receiving structure (6), with the installation and orientation insert (7) not extending beyond the convex outer anchoring surface (2),
   e) bringing the installation and orientation insert (7) back to room temperature in order to reduce the dimensions thereof, so as to achieve a radial clamping of the peripheral annular fixing structure (10) on the outer annular receiving structure (6),
   wherein the outer annular receiving structure (6) comprises a continuous or interrupted peripheral radial shoulder (d) of an annular edge (4), and the receiving face (9) of the outer annular receiving structure (6) has a locking groove (14, 16) or a locking rib (17).

2. The method as claimed in claim 1, wherein:
   the concave inner receiving face (3) is a sphere portion having an opening face (5) contained in an opening plane (P),
   the annular receiving structure (6) is set back from the opening plane (P).

3. The method as claimed in claim 1, wherein the method additionally has a step f) during which a unit resulting from step (e) and packed in a microbial protection envelope is sterilized.

4. The method as claimed in claim 3, wherein step f) of sterilization is carried out by bombardment with gamma rays.

5. The method as claimed in claim 1, wherein the installation and orientation insert (7) is made of polyethylene.

6. The method as claimed in claim 1, wherein:
the outer annular receiving structure (6) comprises a continuous or interrupted peripheral radial shoulder (d) of the annular edge (4), with a receiving face (9) directed radially outwardly,
the installation and orientation insert (7) has a continuous or interrupted peripheral annular fixing structure (10).

7. The method as claimed in claim 6, wherein:
the locking groove (14) of the receiving face (9) of the outer annular receiving structure (6) is an interrupted peripheral locking groove (14),
the connecting face (11) of the peripheral annular fixing structure (10) of the installation and orientation insert (7) has a plurality of locking ribs (15a-15d) which are distributed peripherally and are designed so as to engage in the interrupted peripheral locking groove (14).

8. The method as claimed in claim 7, wherein:
the peripheral radial shoulder (d) of the annular edge (4) has a thickness (e1) of greater than or equal to approximately 0.5 mm,
said interrupted peripheral locking groove (14) or said continuous peripheral annular locking groove (16) of the outer annular receiving structure (6) has a radial thickness (e2) of between approximately 0.2 mm and approximately 0.6 mm.

9. The method as claimed in claim 8, wherein the peripheral annular fixing structure (10) of the installation and orientation insert (7) has a radial thickness (e3) substantially equal to or less than the thickness (e1) of the radial shoulder (d) of the annular edge (4).

10. The method as claimed in claim 7, wherein said interrupted peripheral locking groove (14) or said continuous peripheral annular locking groove (16) of the outer annular receiving structure (6) has a height (h2) of between approximately 0.4 mm and approximately 3 mm.

11. The method as claimed in claim 6, wherein:
either the receiving face (9) of the outer annular receiving structure (6) or the connecting face (11) of the peripheral annular fixing structure (10) has a continuous peripheral annular locking groove (16),
the other of the connecting face (11) of the peripheral annular fixing structure (10) or the receiving face (9) of the outer annular receiving structure (6) has a continuous or interrupted peripheral annular locking rib (17) designed so as to engage in the continuous peripheral annular locking groove (16).

12. The method as claimed in claim 6, wherein the peripheral radial shoulder (d) of the annular edge (4) has a height (h1) of between approximately 1 mm and approximately 4 mm.

13. The method as claimed in claim 1, wherein the assembly structure (8) comprises a fixation hole (20) with internal thread (21) made in the installation and orientation insert (7), permitting the screwing of a corresponding threaded portion of the impactor.

14. The method as claimed in claim 13, wherein the fixation hole (20) is a through-hole able to cooperate with a disconnecting tool having a threaded rod which is able to be screwed into the through-hole and which has a distal end designed to bear against the concave inner receiving face (3) of the cup (1) when the threaded rod is screwed into the through-hole.

15. The method as claimed in claim 13, wherein:
the installation and orientation insert (7) is designed in such a way that a free space (E1) remains between the installation and orientation insert (7) and the bottom of the concave inner receiving face (3) once the installation and orientation insert (7) has been fixed to the outer annular receiving structure (6) of the ceramic cup (1),
the installation and orientation insert (7) bears in a sealed manner across the connecting face (11) against the receiving face (9) of the outer annular receiving structure (6),
the fixation hole (20) is a through-hole via which the free space (E1) between the installation and orientation insert (7) and the bottom of the concave inner receiving face (3) is brought into communication with the outside and which is dimensioned for leaktight engagement of the end of a syringe.

16. The method as claimed in claim 1, wherein the ceramic cup (1) has a thickness (e4), near the annular edge (4), which is between approximately 3 mm and approximately 7 mm.

* * * * *